United States Patent [19]

Riemann et al.

[11] Patent Number: 4,638,099

[45] Date of Patent: Jan. 20, 1987

[54] METHOD FOR MAKING 4,4'-DIHYDROXYDIPHENYL ETHER

[75] Inventors: Achim Riemann, Griesheim; Werner Ude, Darmstadt, both of Fed. Rep. of Germany

[73] Assignee: Röhm GmbH, Darmstadt, Fed. Rep. of Germany

[21] Appl. No.: 821,899

[22] Filed: Jan. 23, 1986

[30] Foreign Application Priority Data

Feb. 27, 1985 [DE] Fed. Rep. of Germany ....... 3506845

[51] Int. Cl.$^4$ ..................... C07C 41/26; C07C 43/295
[52] U.S. Cl. ..................................... 568/638; 568/639
[58] Field of Search ........................ 568/638, 639, 770

[56] References Cited

U.S. PATENT DOCUMENTS

| | | |
|---|---|---|
| 2,835,700 | 5/1958 | Boyle et al. ................... 568/639 X |
| 3,886,218 | 5/1975 | Biller et al. ........................ 568/638 |
| 3,920,386 | 12/1976 | Stamatoff . |
| 4,326,088 | 4/1982 | Braus ................................... 568/638 |
| 4,582,944 | 4/1986 | Taniguchi et al. ............. 568/638 X |

OTHER PUBLICATIONS

Chem. Abstr. 78, 29358u.
Chem. Abstr. 55, 2602a.

*Primary Examiner*—Bernard Helfin
*Attorney, Agent, or Firm*—Curtis, Morris & Safford

[57] ABSTRACT

A method for making 4,4'-dihydroxydiphenyl ether from diphenyl ether by oxidatively iodinating diphenyl ether to 4,4'-diiododiphenyl ether and/or 4-hydroxy-4'-iododiphenyl ether, hydrolyzing this product with a base, recovering iodine from the solution containing iodide, and recycling the iodine to the iodination step.

10 Claims, No Drawings

METHOD FOR MAKING 4,4'-DIHYDROXYDIPHENYL ETHER

The present invention relates to a method for making 4,4'-dihydroxydiphenyl ether from diphenyl ether. 4,4'-dihydroxydiphenyl ether of the formula

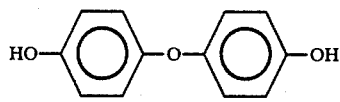

is of interest as an intermediate product, particularly as a difunctional compound for the production of plastics. Up to now unsatisfactory manufacturing processes have militated against the commercial use of this substance in the production of polycondensation resins, for example corresponding polycarbonates, having advantageous properties.

According to Kaloshin et. al., Metody Poluch. Khim. Reaktiv. Prep. 1971, 23, 54–55 (CA 78, 29358u), 4,4'-dihydroxydiphenyl ether is obtained in a yield of 51.5 percent by diazotization of 4,4'-diaminodiphenyl ether followed by decomposition of the diazonium salt with sulfuric acid.

U.S. Pat. No. 3,290,386 describes a method for making 4,4'-dihydroxydiphenyl ether from 4,4'-dibromodiphenyl ether, the latter being hydrolyzed with sodium hydroxide solution in the presence of copper (I) ions and sodium peroxide at a temperature from 185° C. to 190° C. After neutralization with hydrochloric acid, the product of the process is obtained in a nearly quantitative yield.

In the process of Kaloshin et al., the diaminodiphenyl ether used as starting product has to be produced in several reaction steps, the last of these involving the reduction of the corresponding dinitro compound. According to the U.S. patent, the hydrolysis yields, in addition to the desired product, sodium bromide in an aqueous solution as a byproduct. The latter and the hydrobromic acid formed during the production of the starting compound through bromination of the diphenyl ether must be disposed of, which poses serious problems because of the high corrosiveness and difficult handling of hydrogen bromide and of the bromine which may be recovered from it.

Thus, there has been a need for a method for making 4,4'-dihydroxyphenyl ether which uses low cost diphenyl ether as the starting product and auxiliary substances which can be readily worked up and which render the process more economical overall and, in fact, make possible the commercial production of the product.

This need is filled by the process of the invention wherein:
1. Diphenyl ether is iodinated oxidatively, that is without the formation of equivalent amounts of hydrogen halide, in the para positions;
2. the iodination products are hydrolyzed with alkali metal hydroxide;
3. 4,4'-dihydroxydiphenyl ether is liberated by the addition of acid;
4. the iodide is oxidized to iodine in the acidic filtrate; and
5. the iodine, obtained as a solid and readily separated, is recycled to the iodination of the first step.

Aromatic chloro and bromo compounds usually can be readily produced by the direct action of the halogens on appropriate aromatics, which also results in the formation of an equivalent amount of hydrogen halide. An analogous synthesis of aromatic iodo compounds is not possible. The iodination of aromatic compounds is feasible only in the presence of oxidizing agents such as nitric acid, persulfate, or iodic acid. For example, Wirth et. al. Ann. 634 (1960), 84, describe the production of 4,4'-diiododiphenyl ether in a net yield of 71 percent of theory by the action of iodine and iodic acid on diphenyl ether. An iodination variant with bis(trifluoroacetoxy)iodobenzene and iodine as the iodination system is reported by Merkushev et. al., Synthesis 1980, 486, 4,4'-diiododiphenyl ether being obtained in a yield of 79 percent. Both this trivalent organic iodo compound and iodic acid are too expensive as oxidants for commercial use.

It has been found that in the production of paraiodinated diphenyl ethers by the iodination of diphenyl ether, low cost inorganic peroxygen compounds such as ammonium persulfate or sodium persulfate are advantageously used as oxidizing agents, 4,4'-diiododiphenyl ether then being formed in a practically quantitative yield, or the iodination is carried out in the presence of hydrogen peroxide, which will yield mixtures of 4,4'-diiododiphenyl ether and 4-hydroxy-4'-iododiphenyl ether. The direct iodination of aromatic compounds, in this case diphenyl ether in particular, with iodine and oxidants which have sufficient oxidation potential for the oxidation of hydrogen iodide to iodine is here referred to as oxidative iodination.

It has further been found that iodination with hydrogen peroxide as the oxidant requires heavy metal catalysis in addition to the known acid catalysis. Suitable heavy metal catalysts for the purposes of the present invention are those which occur in oxidation states with different valences and can readily be converted to them, for example copper, iron, and cobalt. In the absence of copper, for example, lower conversion will be obtained then in its presence under otherwise comparable conditions.

Moreover, it has been found that the iodination products, 4,4'-diiododiphenyl ether and 4-hydroxy-4'-iododiphenyl ether, are converted quantitatively to the corresponding diphenolate and iodide, from which 4,4'-dihydroxydiphenyl ether is then liberated in known manner by the addition of acid and filtered off, the iodide then being oxidized quantitatively in the filtrate by know commercial processes, for example with $Cl_2$ or $H_2O_2$, to iodine, which is recycled to the iodination step.

The preparation of 4,4'-diiodo- or hydroxyiododiphenyl ethers in accordance with the invention by oxidative iodination of diphenyl ether and their hydrolysis, not described to date, to obtain 4,4'-dihydroxydiphenyl ether represents a route to the production of 4,4'-dihydroxydiphenyl ether that is technically substantially better and more economical than all those up to now combined. One reasons for this is that the halogenation of the diphenyl ether by the process claimed does not yield hydrogen halide as a reaction product. Another reason is that aromatic compounds of iodine are known to be more readily hydrolyzed with aqueous bases. Still other reasons are that the iodine used in the process is recovered quantitatively and, being recovered as a solid, is readily separated and recycled to iodination of the diphenyl ether. In the process of the invention, 4,4'-dihydroxydiphenyl ether is obtained in crude yields of over 90 percent of theory, based on diphenyl ether as the starting product. The inventive process for the production of 4,4'-dihydroxydiphenyl ether is readily manageable with commonly employed technologies through the use of an iodinated intermediate product instead of a brominated one.

The oxidative iodination of diphenyl ether is carried out in the presence of solvents and of strong acids such as mineral acids, trifluoroacetic acid, or so called superacids as catalysts. Those solvents known to be used in iodination reactions, for example alcohols such as methanol, or carboxylic acids such as acetic acid, to which water is added for solubilization of the oxidants in the reaction medium, are suitable for use as solvents. For the graded solubility of the reaction products 4,4'-diiododiphenyl and ammonium bisulfate or ammonium sulfate, as when ammonium persulfate is used as the oxidant, and for their separation by fractional crystallization, a solvent/water mixture tailored thereto and containing about 10 weight percent of water or more is also advantageous. Sulfuric acid is well suited for use as a mineral acid in the acid catalysis of the iodination reaction. It will greatly accelerate the reaction and will not result in side reactions as would hydrochloric acid, for example. The concentration of the acid catalyst should range from 0.1 to 10, and more particularly from 1 to 5, percent by weight of the reaction medium.

The reaction temperature may range from about room temperature to about 100° C. and the reaction time, which is dependent primarily on the reaction temperature and the acid concentration, will range from less than one hour to several hours. For example, diphenyl ether in aqueous acetic acid is converted with sulfuric acid as catalyst with $I_2$ and ammonium persulfate within one hour to diiododiphenyl ether, which at a reaction temperature of 80° C. is not soluble in the reaction medium. The ether is filtered off hot by suction and the filtrate is cooled to room temperature. The ammonium bisulfate formed in the iodination precipitates, possibly in admixture with ammonium sulfate. It is filtered off by suction and the mother liquor is reused in an iodination.

When the iodination is carried out with $H_2O_2$ as oxidizing agent, for example in aqueous acetic acid as the reaction medium, small amounts of copper are used as a catalyst in addition to the mineral acid. The copper may be added as a mixture of powdered copper and cuprous chloride, for example, or may be derived from parts of the reaction vessel which contain copper. The iodination product is obtained in high yields as a mixture of 4,4'-diiododiphenyl ether and 4-hydroxy-4'-iododiphenyl ether in a molar ratio of 1:1, for example, and can then be used as such in the hydrolysis.

The hydrolysis of 4,4'-diiododiphenyl ether and/or 4-hydroxy-4'-iododiphenyl ether is carried out by heating the iodination product, washed with water, in an aqueous alkaline medium having a water content from 10 to 50 weight percent, with copper or copper ion and alkali metal or alkaline earth metal peroxide catalysts, to temperatures ranging from about 100° C. to about 200° C. As bases, essentially strong inorganic bases, and particularly alkali metal and/or alkaline earth metal hydroxides, are used in the reaction in an amount ranging from the stoichiometrically required amount to six times the stoichiometric amount. The copper catalyst and the peroxide catalyst are used in amounts from 1 to 10 weight percent each, based on the 4,4'-diiododiphenyl ether.

The reaction solution, which is cooled after the reaction and further diluted with water, is freed from copper by filtration and then mixed with acid, for example concentrated hydrochloric acid, to obtain a pH value of 7 or less. The 4,4'-dihydroxydiphenyl ether then precipitates and is isolated by filtration. Recrystallization from water yields pure 4,4'-dihydroxydiphenyl ether.

The regeneration of the iodine can be effected quantitatively by oxidation with chlorine, for example as described in Ullmanns Enzyklopaedie der technischen Chemie, 4th ed., vol. 13, p. 423, the iodine being separated as a solid and recycled to the iodination of diphenyl ether.

The Examples which follow will serve to illustrate the invention.

EXAMPLE 1

Oxidative Iodination of Diphenyl Ether with Ammonium Persulfate

In a 2-liter three-neck flask equipped with stirrer, thermometer, and condenser, 76.6 g (0.45 mole) of diphenyl ether and 125.2 g (0.49 mole) of iodine were dissolved in 700 ml of 85% acetic acid, and 143.8 g (0.63 mole) of ammonium persulfate and 25 ml of concentrated sulfuric acid were added. The batch was slowly heated to 80° C. and held at that temperature for one hour. The precipitated 4,4'-diiododiphenyl ether was filtered off hot and the filter cake was washed with hot water and then with a little cold methanol. After the filtrate had cooled, the precipitated ammonium bisulfate was drawn off by suction and the mother liquor was used in further iodinations. The yield of raw 4,4'-diiododiphenyl ether was 198 g (96%). After recrystallization from 2 liters of glacial acetic acid, 137 g (72%) of colorless crystals having a melting point of 138° C. (141° C. in the literature) were obtained.

EXAMPLE 2

Oxidative Iodination of Diphenyl Ether with Hydrogen Peroxide

In a 1-liter four-neck flask equipped with stirrer, thermometer, condenser, and dropping funnel, 34.0 g (0.2 mole) of diphenyl ether and 55.7 g (0.22 mole) of iodine were dissolved in 270 ml of glacial acetic acid. To this there were added 2 g of powdered copper, 1.5 g of cuprous chloride, 24 ml of water, and 12 ml of concentrated sulfuric acid. The batch was heated to 50° C. and 38.0 g (0.28 mole) of 25% hydrogen peroxide solution were added by means of a dropping funnel, 10 g being added at once and the rest dropwise within 1 hour. The batch was stirred for 2 hours at 50° C. After cooling, the precipitated product was drawn off by suction and washed with cold methanol. 59.6 g (81% of theory) of a 1:1 mixture of 4,4'-diiododiphenyl ether and 4-hydroxy-4'-iododiphenyl ether were obtained.

EXAMPLE 3

Preparation of 4,4'-Dihydroxydiphenyl Ether

In a 0.5-liter three-neck flask equipped with stirrer, thermometer, and ball condenser, 84.4 g (0.2 mole) of 4,4'-diiododiphenyl ether, 93.0 g (2.32 moles) of NaOH, 2.1 g of powdered copper, 1.7 g of cuprous chloride, 3.3 g of sodium peroxide, and 33 ml of water were heated over 4 hours to 190° C. After cooling to 140° C., another 37 ml of water were added and the batch was stirred for another 3 hours at 150° C. After cooling to room temperature, the batch was mixed with 200 ml of water and filtered. 200 g of ice were added to the filtrate, which was acidified with concentrated hydrochloric acid. The precipitated 4,4'-dihydroxydiphenyl ether was drawn off by suction and recrystallized from 0.8 liter of water. Yield: 33.5 g (83%).

EXAMPLE 4

Iodine Recovery

The acidic mother liquor from Example 3 was mixed with 50 ml of 30% hydrogen peroxide and the precipitated iodine crystals were drawn off by suction. 46.2 g (91%) of iodine was recovered and recycled to the oxidative iodination step.

What is claimed is:

1. A method for making 4,4'-dihydroxy-diphenyl ether from diphenyl ether, which method comprises
   oxidatively iodinating diphenyl ether;
   hydrolyzing the iodinated diphenyl ether with a base to form diphenyl-ether-4,4'-diphenolate and iodide;
   liberating 4,4'-dihydroxydiphenyl ether in the basic hydrolyzate by the addition of acid thereto;
   oxidizing iodide in the acidic filtrate to iodine; and
   recycling said iodine to the iodination of diphenyl ether.

2. A method as in claim 1 wherein said oxidative iodination is effected with iodine and an inorganic peroxide as the oxidizing agents.

3. A method as in claim 1 wherein said inorganic peroxide is a persulfate and/or hydrogen peroxide.

4. A method as in claim 1 wherein said oxidative iodination is acid catalyzed.

5. A method as in claim 1 wherein said oxidative iodination is effected with hydrogen peroxide as an oxidizing agent in the presence of catalytic amounts of copper and/or copper ions.

6. A method as in claim 1 wherein the iodinated diphenyl ether is hydrolyzed with an inorganic base.

7. A method as in claim 1 wherein the iodinated diphenyl ether is hydrolyzed in the presence of a catalytic amount of copper and/or copper ion and of an alkali metal peroxide or alkaline earth metal peroxide.

8. A method as in claim 1 wherein the iodinated diphenyl ether is hydrolyzed with an alkali metal hydroxide 9. A method as in claim 1 wherein said iodide is oxidized with chlorine to iodine.

10. A method as in claim 1 wherein said iodide is oxidized with hydrogen peroxide to iodine.

* * * * *